United States Patent
Stutz, Jr. et al.

(10) Patent No.: US 7,390,314 B2
(45) Date of Patent: Jun. 24, 2008

(54) LEAD SCREW DRIVEN RESERVOIR WITH INTEGRAL PLUNGER NUT AND METHOD OF USING THE SAME

(75) Inventors: William H. Stutz, Jr., Eagle Rock, CA (US); Herman L. Renger, Calabasas, CA (US); Cary D. Talbot, Santa Clarita, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 659 days.

(21) Appl. No.: 10/379,627

(22) Filed: Mar. 5, 2003

(65) Prior Publication Data

US 2004/0176725 A1 Sep. 9, 2004

(51) Int. Cl.
*A61M 5/20* (2006.01)
*A61M 5/00* (2006.01)

(52) U.S. Cl. .............................. 604/155; 604/211

(58) Field of Classification Search .............. 604/31, 604/65, 64, 154, 155, 153, 131, 187, 181, 604/207–210, 151; 417/18, 474
See application file for complete search history.

(56) References Cited

U.S. PATENT DOCUMENTS

| | | | |
|---|---|---|---|
| 1,751,139 A | 3/1930 | Feinstein | |
| 1,905,569 A | 4/1933 | Rapellin | |
| 2,627,270 A | 2/1953 | Glass | 128/218 |
| 2,853,070 A | 9/1958 | Julliard | 128/218 |
| 4,086,062 A * | 4/1978 | Hach | 422/100 |
| 4,424,720 A | 1/1984 | Bucchianeri | 74/89.15 |
| 4,769,009 A | 9/1988 | Dykstra | 604/155 |
| 5,704,912 A * | 1/1998 | Lawrence et al. | 604/97.02 |
| 5,921,967 A * | 7/1999 | Sadowski et al. | 604/218 |
| 5,954,697 A | 9/1999 | Srisathapat et al. | 604/155 |
| 6,659,980 B2 * | 12/2003 | Moberg et al. | 604/154 |
| 2001/0034520 A1 * | 10/2001 | Moberg et al. | 604/154 |
| 2002/0029017 A1 | 3/2002 | Neer et al. | 604/131 |
| 2002/0173769 A1 | 11/2002 | Gray et al. | |
| 2003/0009133 A1 * | 1/2003 | Ramey | 604/155 |

FOREIGN PATENT DOCUMENTS

EP 1219312 7/2002

OTHER PUBLICATIONS

PCT International Search Report for International Application No. PCT/US2004/008503.

* cited by examiner

*Primary Examiner*—Matthew F Desanto

(57) ABSTRACT

An improved reservoir is provided for use in a medication infusion device for operating the reservoir to administer a fluid to a patient. The reservoir comprises a hollow barrel adapted to receive a supply of fluid for delivery through infusion tubing or the like to the patient, in combination with a reservoir plunger. The reservoir plunger is designed to engage a motor-driven lead screw of the medication infusion device. The reservoir plunger has an integral split nut connector formed on the end of the plunger, which is in co-axial alignment with the lead screw whereby the split nut connector can be engaged directly to the lead screw.

17 Claims, 7 Drawing Sheets

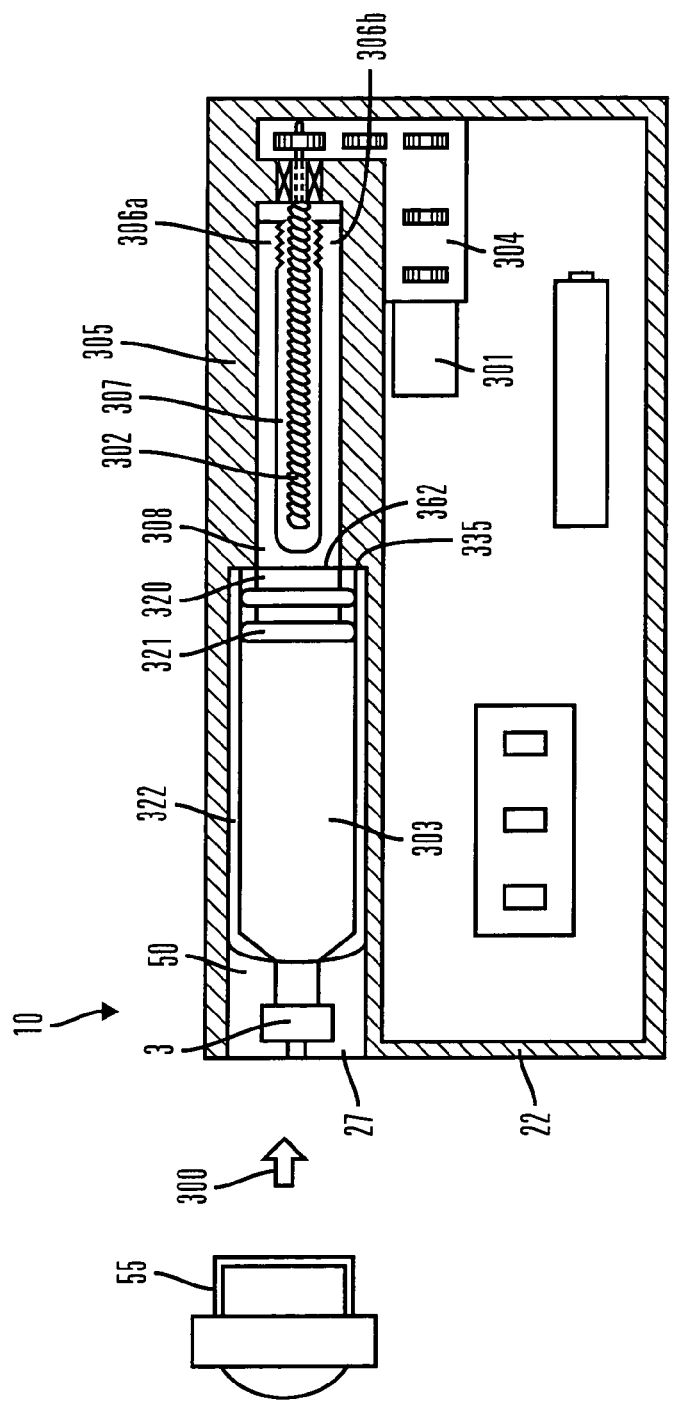
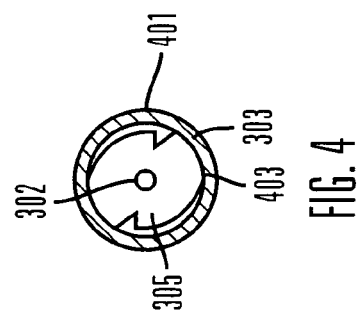
FIG. 3
FIG. 4

Load Position

Engaged Position

LEAD SCREW DRIVEN RESERVOIR WITH INTEGRAL PLUNGER NUT AND METHOD OF USING THE SAME

FIELD OF THE INVENTION

This invention relates generally to improvements in medication-containing reservoirs and related infusion devices for controlled delivery of a selected medication from the reservoir to a patient. More particularly, this invention relates to an improved reservoir plunger adapted for direct drive connection with the infusion device.

BACKGROUND OF THE INVENTION

Infusion devices and systems are relatively well known in the medical arts, for use in delivering or dispensing a prescribed medication such as insulin to a patient. In one form, such devices comprise a relatively compact housing adapted to receive and support a reservoir carrying the prescribed medication for administration to the patient through infusion tubing and an associated catheter or the like. The infusion device includes a small drive motor connected via a lead screw assembly for motor-driven advancement of a reservoir piston plunger to deliver the medication to the patient. A programmable controller can be provided for operating the drive motor continuously or at periodic intervals to obtain a closely controlled and accurate delivery of medication over an extended period of time. Such infusion devices are utilized to administer insulin and other medications, with exemplary device constructions being shown and described in U.S. Pat. Nos. 4,562,751; 4,678,408; 4,685,903; 5,080,653; 5,097,122; and 5,505,709, which are incorporated by reference herein.

Infusion devices of the general type described above have provided significant advantages and benefits with respect to accurate delivery of medication or other fluids over an extended period of time. The infusion device can be designed to be extremely compact as well as water resistant, and may thus be adapted to be carried by the user, for example, by means of a belt clip or the like. As a result, important medication can be delivered to the user with precision and in an automated manner, without significant restriction on the user's mobility or life-style.

These devices often incorporate a drive system that uses a lead screw coupled to motors. The motors can be of the DC, stepper or solenoid varieties. These drive systems provide an axial displacement of the reservoir or reservoir piston to dispense the medication to the user. Powered drive systems are advantageous since they can be electronically controlled to deliver a predetermined amount of medication.

FIG. 1 shows a lead screw arrangement that is known in the art. Located in a housing 107, a motor 101 drives a lead screw 102 that has threads, which are engaged with a drive nut 103. Thus, the rotational force of the lead screw 102 is transferred to the drive nut 103 that causes it to move in an axial direction d. Because the drive nut 103 is fixably attached to a reservoir piston 104, it likewise will be forced in an axial direction d', parallel to direction d, thus dispensing the fluid from the reservoir 105 into the infusion set 106.

FIG. 2 shows a different lead screw arrangement that is also known in the art. In this arrangement, a motor 201 (or a motor with an attached gear box) has a drive shaft 201a that drives a set of gears 202. The torque is then transferred from the gears 202 to a lead screw 203. The threads of the lead screw 203 are engaged with threads [not shown] in a plunger slide 204. Thus, the torque of the lead screw 203 is transferred to the slide 204 which causes it to move in an axial direction d', parallel to the drive shaft 201a of the motor 201. The slide 204 is in contact with a reservoir piston 205 which likewise will be forced to travel in the axial direction d' thus dispensing fluid from the reservoir 206 into the infusion set 207. The assembly can be contained in a housing 208.

In the operation of these infusion device systems, the reservoir piston will be fully advanced when virtually all of the fluid in the reservoir has been dispensed. In certain infusion device mechanism (e.g. DC motor and/or stepper motor configurations), the axial displacement of a piston engagement with the motor lead screw (e.g. a nut) is also typically fully displaced when the reservoir is near empty. In these devices, to insert a new reservoir that is full of fluid, it is necessary to reverse the direction of the lead screw until the piston engagement returns back to the starting position. Thus, the drive system must be able to be reversed in direction. On the other hand, in solenoid based drive systems, the piston engagement must be reset manually when placing in a new full reservoir. Both types of reset methods are problematic. For example, in motor rewind configurations, the motor must be capable of being reversed requiring additional switches and more complex circuitry. In addition, home positioning "sensing" is required to shut off motor at home position, extra battery energy is consumed, such configurations do not accommodate a partially filled reservoir, etc. Similarly, manual reset configurations also have inherent problems. Typically, manual reset configurations require a more complex housing to accommodate an access to the lead screw/nut area (e.g. a hatch or a slot paralleling the lead screw). In addition, the disengageable nut is both difficult and costly to design and manufacture, the disengagement function must be safeguarded from any inadvertent actuation, additional wear issues must be considered, manual dexterity limits exist, etc.

SUMMARY OF THE DISCLOSURE

Embodiments of the present invention provide an improved reservoir/lead screw arrangement, which obviates for practical purposes the above-mentioned limitations.

According to an embodiment of the invention, an improved reservoir for use with a medication infusion device having a rotatable lead screw for controllably dispensing fluid from the reservoir is described. The reservoir includes a hollow reservoir barrel adapted for receiving and supporting a supply of fluid and a reservoir plunger slidably received into the barrel and movable within the barrel to deliver the fluid. The reservoir plunger has an integral split nut connector in co-axial alignment with the lead screw formed on the end of the plunger so that the split nut connector can be engaged directly to the lead screw. In particular embodiments, the reservoir plunger includes a slot and two legs and the integral split nut connector includes a half nut formed at the end of each leg of the plunger such that the lead screw can fit inside the slot and the half nut on each leg can simultaneously engage the lead screw. In addition, the half nuts are engaged to the lead screw by a camming receptacle, where the camming receptacle has camming surfaces to press the half nuts together to form a whole nut structure over the lead screw when the plunger is twisted within the camming receptacle. In additional embodiments, the reservoir can be engaged to the lead screw at any fill level. In further embodiments, the medication infusion device is unidirectional drive system. Moreover, in still further embodiments, a locking cap is used to lock the reservoir inside the medication infusion device and engage the reservoir to the lead screw. The locking cap can also serve to make the medication infusion device water resistant.

According to another embodiment of the invention, a method of placing a reservoir in a medication infusion device having a rotatable lead screw for controllably dispensing fluid from the reservoir an infusion device system is provided. The method includes forming an integral split nut connector on a rear end of the plunger; aligning coaxially the split nut connector with the lead screw; and engaging the split nut connector directly to the lead screw.

In addition, according to another embodiment of the invention an infusion device system is described. The system contains a reservoir having a reservoir barrel adapted to be filled with a fluid, and a reservoir plunger slidably received into the barrel and movable within the barrel to deliver the medication from the reservoir barrel, an infusion device including a device housing defining a reservoir compartment for receiving and supporting the reservoir, and a drive to engage and controllably move the plunger to deliver the medication from the reservoir, the drive means including a rotatably driven lead screw, where the reservoir plunger has an integral split nut connector in co-axial alignment with the lead screw formed on the end of the plunger whereby the split nut connector can be engaged directly to the lead screw.

Other features and advantages of the invention will become apparent from the following detailed description, taken in conjunction with the accompanying drawings, which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIG. 3 is a side plan, cut-away view of a plunger/lead screw arrangement in accordance with an embodiment of the present invention;

FIG. 4 is a cross-sectional top view of the camming receptacle in accordance with an embodiment of the present invention;

DETAILED DESCRIPTION OF THE PREFERRED EMBODIMENTS

Figure 1:
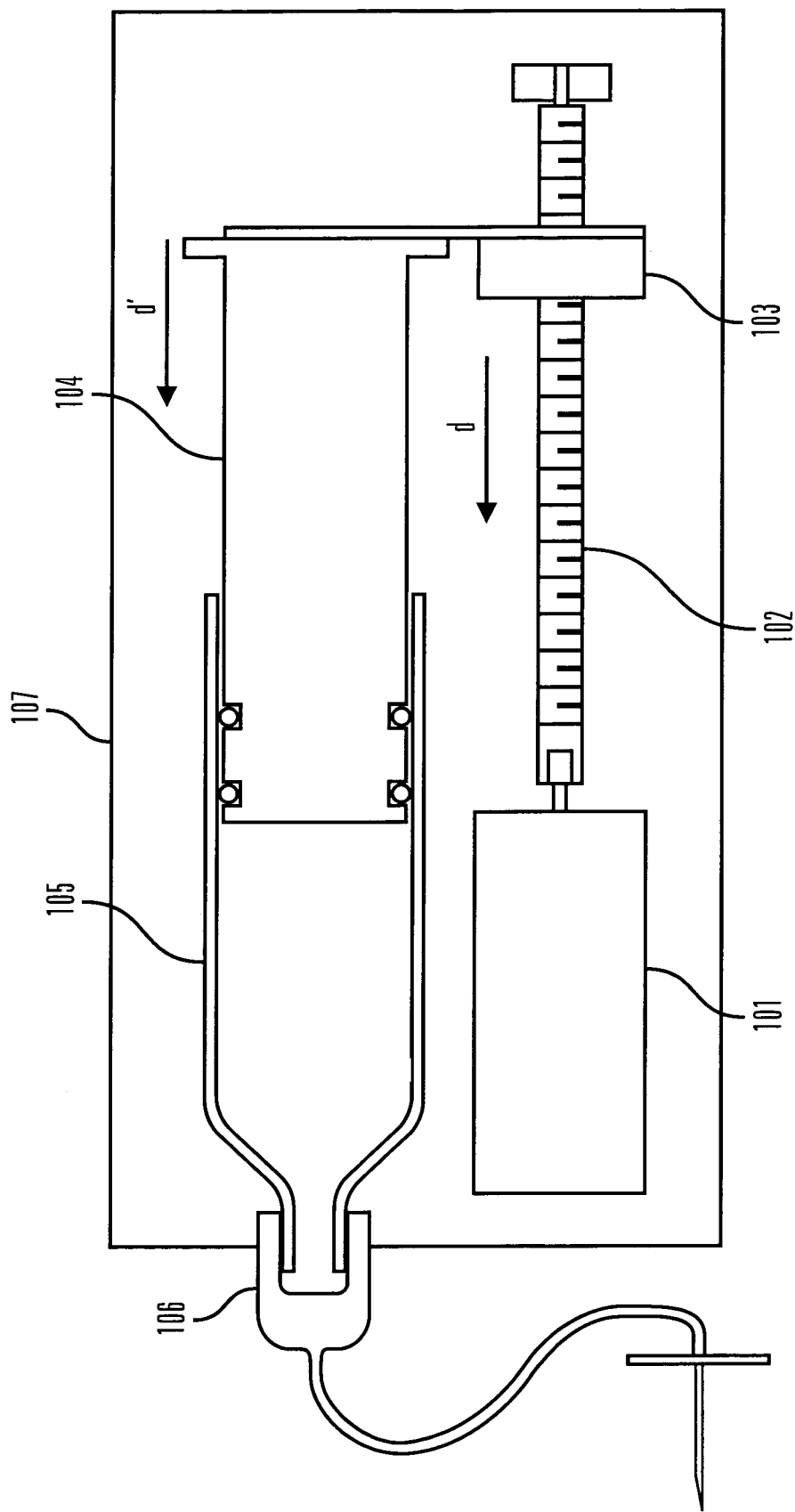
FIGS. 1 and 2 are side plan views of exemplary lead-screw drive mechanisms known in the prior art.
Figure 2:
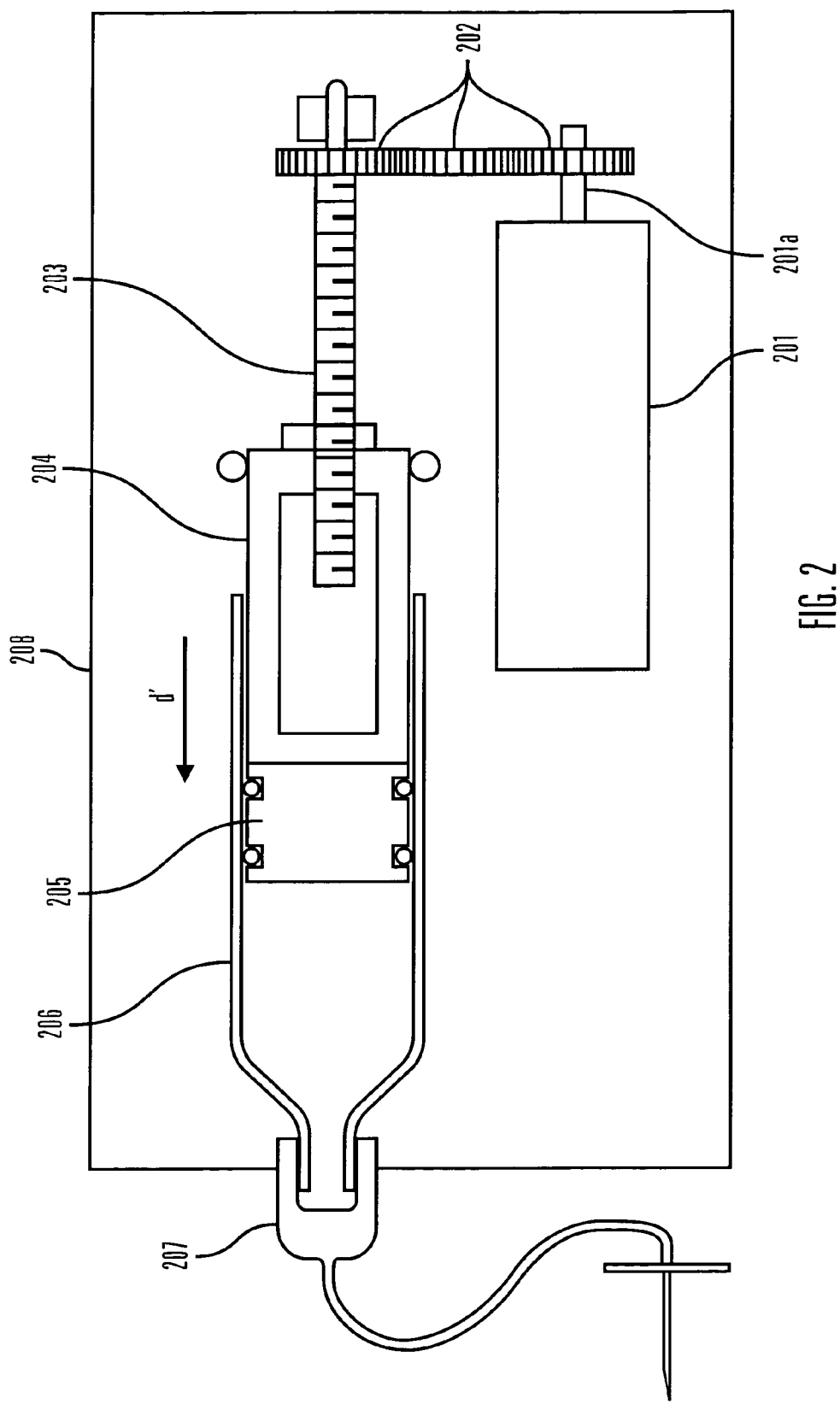

Embodiments of the present invention are directed to an improved lead screw/reservoir plunger arrangement for use in infusion devices. As shown in FIG. 3, the invention is preferably embodied in an external infusion device 10 for infusion of a liquid, such as medication, chemicals, enzymes, antigens, hormones, vitamins or the like, into a body of a user. In preferred embodiments of the present invention, the external infusion device 10 is an external infusion pump provided for controlled administration of a selected medication to a patient. Particular embodiments are directed towards use for humans; however, in alternative embodiments, the external infusion devices may be used for animals.

The infusion device 10 is adapted to receive and support a medication-containing reservoir 303 (FIG. 3), and includes electronics and a drive mechanism for automatically and programmably forcing fluid from the reservoir 303 to deliver the medication through infusion tubing (not shown) or the like to the patient (not shown). Programming information can be stored locally on the infusion device 10 and/or remotely sent by a remote commander (not shown). An example of how the programming of the infusion device 10 is performed can be found in U.S. patent application Ser. No. 09/334,858 entitled "External Infusion Device with Remote Programming, Bolus Estimator and/or Vibration Alarm Capabilities" filed on Jun. 16, 1999, which is incorporated by reference herein. In addition, safety circuits and other safety related features are provided in the infusion device 10 to check proper operation of the infusion device 10 and controlled failure in case the infusion device 10 fails. Examples of safety related features can be found in U.S. patent application Ser. No. 10/013,943, entitled "Selective Potting For Controlled Failure and Electronic Devices Employing the Same" filed on Dec. 7, 2001, which is incorporated by reference herein.

In preferred embodiments, the reservoir 303 is a disposable, pre-filled reservoir (pre-filled with insulin or other drug or fluid), however, the improved lead screw/reservoir plunger arrangement can be used in user fillable cartridges, reservoirs or the like. The infusion device 10 has an overall construction and operation that is generally known in the art. Typically, the infusion device 10 includes a relatively compact device housing 22 defining an elongated reservoir compartment 50 adapted to receive and support the reservoir 303. The reservoir 303 includes a reservoir barrel 322 and a reservoir plunger 320. In the preferred embodiments, the reservoir compartment 50 does not form an air tight fit with the exterior of the reservoir barrel 322. Instead, the reservoir compartment 50 leaves enough room for the reservoir 303 to be moved within the reservoir compartment 50 to allow the reservoir plunger 320 to engage the drive system of the infusion device 10.

As seen in FIG. 3, in accordance with preferred embodiments of the present invention, reservoir 303 is loaded through an outlet end 27 into the reservoir compartment 50, as shown marked by the arrow 300. By inserting the reservoir 303 through the outlet end 27, the reservoir 303 is loaded in co-axial alignment with a lead screw 302, which is part of the drive mechanism of the infusion pump 10. When the reservoir 303 is slid into the reservoir compartment 50, the reservoir barrel 322 fits inside the reservoir compartment 50 and the aft end 362 of the reservoir barrel 322 is stopped by a compartment stop 335. By placing the compartment stop 335 at the end of the reservoir compartment 50, the reservoir compartment 50 is able to fit the entire reservoir barrel 322 within the reservoir compartment 50, while allowing the reservoir plunger 320 to extend into a camming receptacle 305.

FIG. 4 is a cross-sectional view of the camming receptacle 305 according to the preferred embodiments of the present invention. As seen in FIG. 4, the inner diameter 403 and the outer diameter 401 of the reservoir 303 remain outside the camming receptacle 305 as stopped by the compartment stop 335 (not seen in FIG. 4). However, the camming receptacle 305 (as best seen in FIG. 3) can accept the reservoir plunger 320 at any length. An important feature of this arrangement is to allow the drive mechanism of the infusion device 10 to load a reservoir 303 at any fill level since the length of the plunger 320 extending out of the reservoir barrel 322 does not impact the placement of the reservoir 303 within the reservoir compartment 50 or the plunger 320 within the camming receptacle 305. The plunger 320/lead screw 302 engagement will be discussed below in more detail with respect to FIG. 6.

Figure 5:
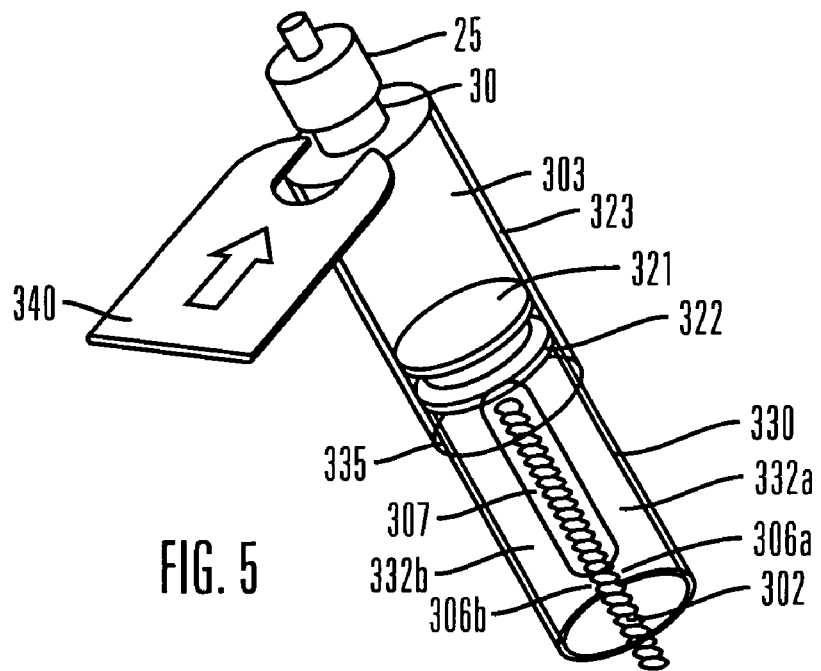
FIG. 5 is a perspective view of a plunger/lead screw arrangement in accordance with an embodiment of the present invention.

In preferred embodiments, the reservoir plunger 320 further includes an elongated piston rod 308 having a generally circular cross-sectional shape containing a slot 307, as best seen in FIG. 5. The slot 307 causes the piston rod 308 to have two legs 332a and 332b. A half split nut 306a, 306b is formed on the end of each leg 332a, 332b of the piston rod 308, where each half 306a, 306b in combination takes a shape of and functions as a whole split nut 306a, b. The slot 307 and split nut 306a, b provide for a drive connection with the motor-driven lead screw 302 of the infusion device 10, as described in more detail below. The legs 332a, 332b along with the split nuts 306a, 306b are designed to be highly flexible in a radial direction but rigid axially. In the preferred embodiments, the desired characteristics of the legs 332a, 332b are achieved by creating arched surfaces on each leg 332a, 332b to strengthen the legs in the axial direction, but still allow flexibility radially.

The reservoir plunger 320 engages the lead screw 302 such that piston rod 308 fits over the lead screw 302 within the slot 307, without contacting the lead screw 302. Once the lead screw 302 is within the slot 307, the legs 332a, 332b are pressed together by a camming receptacle 305 to engage each half 306a, 306b with the lead screw 302 to engage the piston rod 308 with the lead screw 302. The threaded halves of the split nut 306a, b are sized and the threads 310a, 310b are configured for mating engagement with the lead screw 302 once the plunger 320 is engaged with the lead screw 302.

Figure 6:
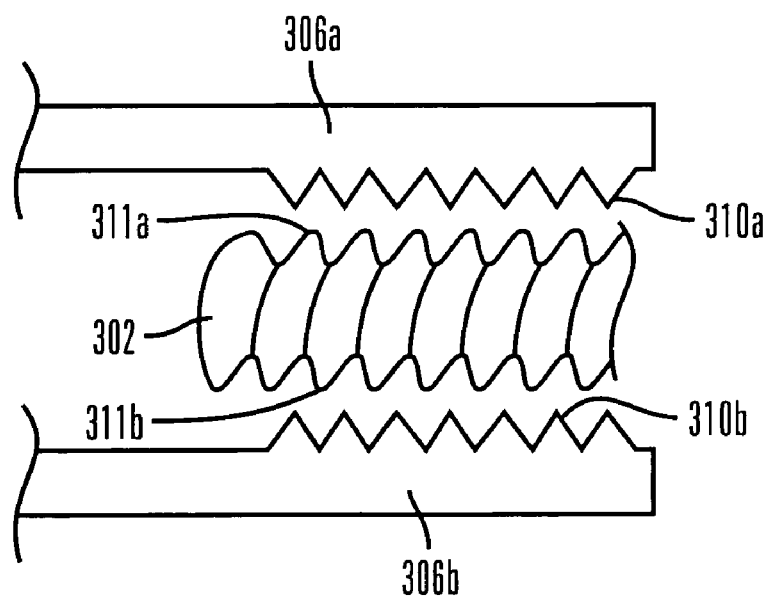
FIG. 6 is a close-up cross-sectional view of the half split-nuts/lead screw arrangement in accordance with an embodiment of the present invention.

FIG. 6 shows a cross-sectional view of the lead screw 302 and half split nuts 306a, b before the split nut 306a, b is engaged to the lead screw 302 according to the preferred embodiments of the present invention. Although the thread profiles on the lead screw 302 and half split nuts 306a, b can be varied, FIG. 6 shows exemplary thread profiles where half split nut threads 310a, 310b tend to be sharp while the lead screw threads 311a, 311b tend to be slightly rounded on top. This thread configuration provides for the situation where even if the peak of the threads 310a, 310b are faced with the peaks of the lead screw 302 that the lead screw 302 and the half split nuts 306a, 306b can still engage one another. The rounded peaks on the lead screw threads 311a, 311b act as camming surfaces when the split nut 306a, 306b is engaged to the lead screw 302 by the camming receptacle 305. In addition, the slightly rounded lead screw threads 311a, 311b act to prevent the metal lead screw threads 311a, 311b to cut into half split nut threads 310a, 310b, which are preferably made from plastic. The workings of the camming receptacle 305 and the engaging mechanism will be discussed in more detail with respect to FIGS. 7a and 7b. The reservoir plunger 320, including the head 321, the piston rod 308, the slot 307 and the split nut 306a, b, is preferably constructed as an integral or one-piece plastic molding. Alternatively, the head 321 and the piston rod 308 can be constructed from separate pieces, where the piston rod 308 can be screwed or otherwise attached onto the head 321 to form the complete reservoir plunger 320.

Figure 7A:
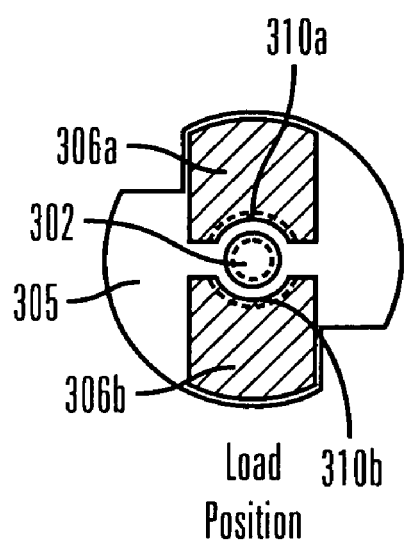
FIGS. 7a and 7b are a cross-sectional top view of a locking mechanism between the plunger and the lead screw, in accordance with the preferred embodiments of the present invention.
Figure 7B:
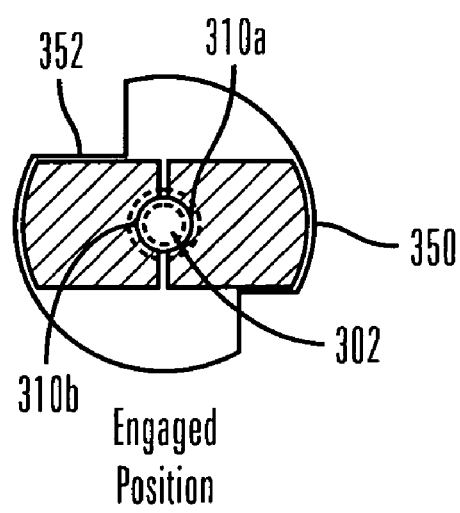

FIGS. 7a and 7b are cross-sectional end views of a locking mechanism between the plunger 320 and the lead screw 302 using the integral split nut 306a, b, in accordance with the preferred embodiments of the present invention. In accordance with one aspect of the invention, the integral split nut 306a, b is engaged to the lead screw 302 by inserting the split nut 306a, b into a camming receptacle 305 and giving the reservoir 303 and/or plunger 320 a clock-wise locking quarter turn. Typically, the lead screw 302 will have threads which drive the plunger 320 in same direction as the locking quarter turn (i.e. clock-wise) in order to ensure that the split nut 306a, b will not disengage during the movement of the lead screw 302. In alternative embodiments, the reservoir 303 can be engaged and disengaged in the reverse direction (i.e. a counter-clockwise turn to engage, and a clockwise turn to disengage).

FIG. 7a shows a top cross-sectional view of the split nut 306a, b disengaged from the lead screw 302 before the clockwise quarter turn. The legs 332a, 332b of the plunger 320 are flexible enough to allow each half split-nut 306a, 306b of the plunger rod 308 to engage the lead screw 302 and form a functional split nut 306a, b over the lead screw 302 as seen in FIG. 7b. As seen in FIG. 7a, the shape of the camming receptacle 305 is such that ends of the plunger 320 can fit in one loading position (i.e. where the walls of the camming receptacle 305 is not cammed). If the one loading position is not used, the plunger legs 332a, 332b cannot fit within the camming receptacle 305 and reservoir 303 would not fit completely within the reservoir compartment 50 indicating an improper installation of the reservoir 303. In alternative embodiments, there can be additional switches and contacts that indicate proper alignment and installation of the reservoir piston 308 within the camming receptacle 305. From the loading position, the camming surfaces 350 on the camming receptacle 305 become radially smaller in a clock-wise direction, such that a clock-wise quarter turn will compress the plunger rod 308 to engage and lock the half split-nuts 306a, 306b over the lead screw 302 within the camming receptacle 305. Preferably, limit stops 352 at 90° act as anti-rotational features for the nut 306a, b relative to the lead screw 302. In addition, position indicators on the legs 332a, 332b and use of a window in the case (not shown) could be used to tell the user when the plunger 320 has been properly rotated into position. In alternative embodiments, the limit stops can be located at different locations or do not exist at all. In addition, there can be other methods of indicating proper locking of the half nuts 306a, 306b on the lead screw 302 such as a special window to only show the legs when the half nuts 306a, 306b have been locked onto the lead screw 302, a switch that would not be activated until the cartridge is rotated into the correct position, or no indicator can exist at all.

In alternative embodiments, the half nuts 306a and 306b need not necessarily form a whole nut 306a, 306b, but may merely balance the force provided by the other half nut. In other words, the half nuts 306a, 306b do not have to be 180° in shape to form a complete 360° whole nut. In addition, in alternative embodiments, there can be more than two partial nuts and more than two legs on the plunger 320. When more than two legs exist, than the camming receptacle 305 would have more than two camming surfaces to engage the multiple legs to lead screw 302. In further embodiments, the camming receptacle 305 may be configured to engage a single leg with one half nut to the lead screw 302.

In preferred embodiments, a locking cap 55 is used to lock the reservoir 303 within the reservoir compartment 50 and to connect infusion tubing (not shown) to the reservoir 303. The outlet end 27 is specifically configured to mate with the locking cap 55. Typically, the interior diameter of the outlet end 27 will have female threads that engage the male threads on the external diameter of the locking cap 55. Thus, the cap 55 can be connected directly onto the reservoir 303 and can be used to lock the reservoir 303 within the reservoir compartment 50 once the locking cap 55 is matted to the outlet end 27. Once the locking cap 55 is mated to the outlet end 27, in preferred embodiments, the infusion device 10 becomes water resistant, preventing water from entering the reservoir compartment 50. Moreover, the locking cap 55 acts as a fluid conduit between the reservoir 303 and the infusion tubing for delivery of the medication by a catheter and infusion set (not shown), or the like, to the patient.

In addition, mating the locking cap 55 to the outlet end 27 can also serve to engage the reservoir plunger 320 to the lead screw 302. The twisting of the locking cap 55 to attach the locking cap 55 to the outlet end 27 can be used at the same time to twist the plunger 320 within the camming receptacle 305 as described with respect to FIGS. 7a and b. However, if the cap 55 is connected directly to the reservoir 303 before inserting the reservoir 303 into the reservoir compartment 50 and the cap 55 is used to engage the plunger 320 to the lead screw 302, the cap will require an additional turn beyond the clock-wise locking quarter turn to lock the cap 55 onto the outlet end 27. In this case, once the plunger 320 is engaged to the lead screw 302, the remaining turn of the reservoir 303 (beyond the clock-wise locking quarter turn would be performed by the plunger head 321 rotating radially within the reservoir barrel 322.

Figure 8:
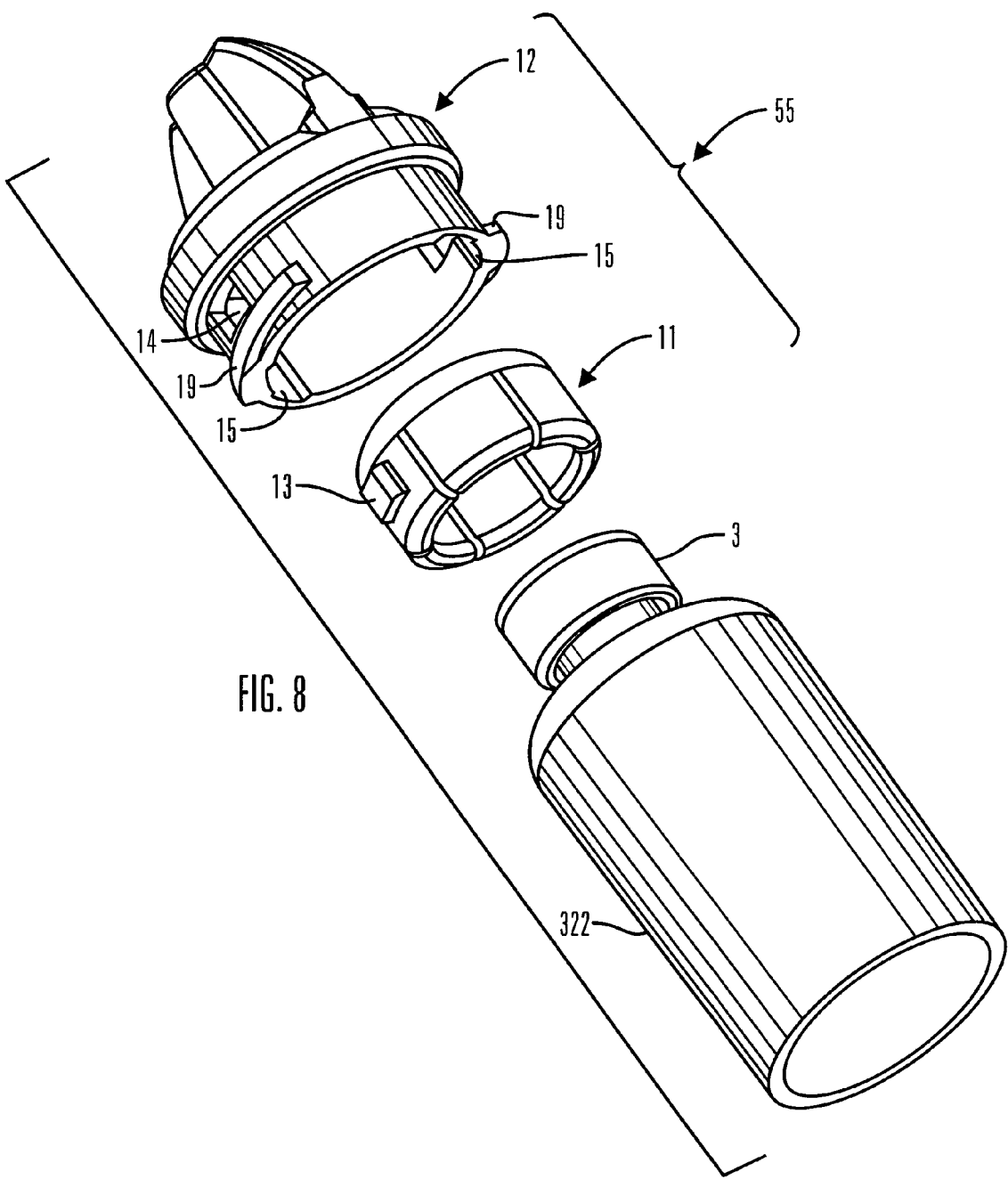
FIG. 8 is a perspective exploded view of the locking cap in accordance with an embodiment of the present invention.

An example of a possible locking cap is a proprietary connector generally described in U.S. patent application Ser. No. 09/428,818 entitled "Reservoir Connector," which is incorporated by reference herein. Accordingly, the preferred embodiment of the locking cap 55 is seen in FIG. 8, where the locking cap 55 includes a base 11 and a cap 12. The cap 12 includes a needle (not shown) located internal to the cap housing. The base 11 would normally be fixedly attached to the reservoir 303 by securing it around the swage 3. However, alternative embodiments of the present invention include a removable base so that the connector interface could be used with standard reservoirs, cartridges or syringes that were not initially manufactured with the base attached.

The cap 12 portion of the locking cap 55 is removably attached to the base 11 with a releasable coupler. In this embodiment, the releasable coupler includes detents 13 formed on the base 11 and detent openings 14 disposed in the cap 12. Two detents 13 are disposed on the sides of the base 11 and are spaced 180° radially apart. Only one detent 13 is shown in FIG. 8. The detents 13 are sized to fit in two detent openings 14 which are formed in the cap 12. As with the pair of detents 13, each of the detent openings 14 is radially spaced apart by 180°.

In operation, the base 11 and the reservoir 303 form an integrated unit, which in turn is to be connected to the cap 12. In connecting this integrated base/reservoir unit to the cap 12, the base 11 is inserted into the lower end of the cap 12. The detents 13 slide into matingly shaped and longitudinally open entry slots 15 formed within the interior walls of the cap 12. When the base 11 is fully inserted in the cap 12, the leading edges of the detents 13 abut an annular stop shoulder (not shown) formed within the cap 12. After the detents 13 are in this position, the base 11 is rotated within the cap 12 toward a locked position. This rotation displaces the detents 13 in a rotational direction for engagement with cam surfaces (not shown) formed within the cap 12. The rotational force on the detents 13 over the cam surfaces provides a compression force on the detents 13. Continued rotation of the base 11 displaces the detents 13 past the cam surfaces and into alignment with the detent openings 14. The detents 13 enter the detent openings 14 with a snap-action. Thus, the detents 13 are effectively locked within the detent openings 14 to prevent longitudinal separation of the base 11 from the cap 12.

In the preferred embodiment, the internal needle (not shown) of the cap 12 is disposed so that when the base/reservoir unit is fully inserted in the cap 12, the needle pierces the septum (not shown) of the reservoir 303. Thus the insertion force of the base/reservoir unit to the point where the detents 13 abut the annular stop shoulder 16 causes the needle to pierce the septum, thus permitting the fluid in the reservoir to flow into the needle and the insertion set tubing (not shown).

After this connection is made, the reservoir, base and cap form a unit that can be releasably secured in the housing of a medication infusion pump 10. The cap 12 includes external threads 19 which are used to engage the threads of the pump housing in order to secure the reservoir/base/cap unit into the housing. In the preferred embodiment, the threads 19 have an eight threads per inch ("TPI"), 2 start profile. Moreover, they have a square shaped cross section that maximizes their holding strength. Other thread profiles and cross-sections may be used however.

When disconnection of the base 11 from the cap 12 is desired, the base 11 must be reverse-rotated within the cap 12, to move the detents 13 past the cam surfaces into re-alignment with the entry slots 15. Such reverse-rotation of the coupler can be performed relatively easily, but essentially requires an affirmative intent by the user to disconnect the coupling. When the detents 13 are re-aligned with the entry slots 15, the cap 12 and base 11 can be separated easily with minimal longitudinal force.

In alternative embodiments, other mechanisms can be used lock the reservoir 303 within the reservoir compartment 50. For example, as shown in FIG. 5, instead of a locking cap 55, a captivating slide 340 can be used to hold the reservoir 303 inside the reservoir compartment 50 after the reservoir 303 is inserted and engaged with the lead screw 302. Similarly, the reservoir 303 can be connected to catheters, needles, infusion sets or the like without a locking cap 55 by using other known connectors such as a luer connector. The luer connection can be modified to perform the same functions as a locking cap 55, without using the proprietary connection of the preferred embodiments.

On the opposite end from the infusion tubing connection, the reservoir plunger 320 of the reservoir 303 extends from the rear (or aft end) 362 of the reservoir barrel 322, and is advanced into the barrel 322 to deliver the medication. As best seen in FIG. 5, the head 321 of the reservoir plunger 320 is generally a cylindrical plug having one or more seal rings 323 for slidably and sealingly engaging the interior of the reservoir barrel 322. Alternatively, the reservoir plunger 320 may use an elastomeric cap instead of the seal rings and/or the head 321 might be a separate component rather than an integrated part of the reservoir plunger 320. The preferred head 321 of the reservoir plunger 320 is described in U.S. patent application Ser. No. 09/698,783 entitled "Improved Fluid Reservoir Piston" filed on Oct. 27, 2000, which is incorporated by reference herein. Regardless of the material used to form the head 321, the friction between the contact surface of the head 321 and the inner surface of the reservoir barrel 303 must be great enough that the plunger 320 does not simply spin within the reservoir barrel 303 when the reservoir barrel is rotated by the user when engaging the plunger 320 to the lead screw 302. However, at the same time, the friction between the contact surface of the head 32 and the inner surface of the reservoir barrel 303 must be minimized to limit the force required to push the plunger 320 inside the barrel 322 and to also allow easy occlusion detection such that any increase of force required to push the plunger 320 inside the barrel 322 can be detected. An example of an occlusion detection scheme which can be used in conjunction with the present application can be found in U.S. Pat. No. 6,485,465 entitled "Methods, Apparatus, and Uses for Infusion Pump Fluid Pressure and Force Detection" which is incorporated by reference herein.

From this engaged position, programmed rotation of the lead screw 302 axially advances the reservoir plunger 320 for programmed delivery of the medication to the patient. It is important to note that once the half nuts 306a, b have been locked onto the lead screw 302, and the reservoir 303 is locked within the reservoir compartment 50, the barrel 322 is locked in position so that it can not move in an axial direction away from the plunger 320. During normal operation of the infusion device, the lead screw 302 is rotatably driven by a drive motor 301 to axially advance the plunger 320 within the reservoir barrel 322 to dispense the medication in a precision controlled manner. As the lead screw 302 is rotatably driven by the drive motor 301, the nut 306a, b moves along the thread engagement of the lead screw 302, which translates into a linear lateral movement of the plunger 320 inside the reservoir barrel 322. As the plunger 320 is inserted into the reservoir barrel 322, the medication is dispensed out of the infusion tubing or the like, out of the opposite end of the reservoir 303. Moreover, because the cam shape of the camming receptacle 305 runs the entire length of the plunger 320, the half nuts 603a, b remain closed around the lead screw 302 as the nut 306a, b moves along the thread engagement of the entire lead screw 302. In particular embodiments, the motor 301 and the lead screw 302 will be connected through a set of gears 304. The particular programmed operation of the device can be set and revised as known in the art, with exemplary pump constructions being shown and described in U.S. Pat. Nos. 4,562,751; 4,678,408; 4,685,903; 5,080,653 and 5,097,122, and U.S. patent application Ser. No. 09/813,660 entitled "Control Tabs for Infusion Devices and Methods of Using The Same" filed on Mar. 21, 2001, which are incorporated by reference herein. The direct drive connection is designed to assure positive and proper operation of the reservoir 303 and further to insure that the reservoir 303 is fully and properly installed into the infusion device 10.

When the user desires to remove the reservoir 303 from the infusion device 10 (typically when the reservoir 303 reaches or nears an empty condition, although the reservoir can be removed at any fill level), the user can unlock the cap 55 from the outlet end 27 and give the reservoir 303 a counter-clockwise unlocking quarter turn. Typically, the unlocking turn will be in the opposite direction of the axial advancement of the plunger along the threads of the lead screw 302 (i.e. counter-clockwise turn). In alternative embodiments, where the lead screw advances the plunger in the opposite direction (i.e. counter-clockwise), the locking and unlocking turns would be reversed from the described embodiments. Once the split nut 306a, b is unlocked, the split nut 306a, b separates into two halves 306a, 306b by the inherent spring action of the legs 332a, 332b of the plunger rod 308 returning to their original positions. Thus, the split nut 306a, b is disengaged from the lead screw 302 and the reservoir 303 can be removed from the reservoir compartment 50.

Figure 9:
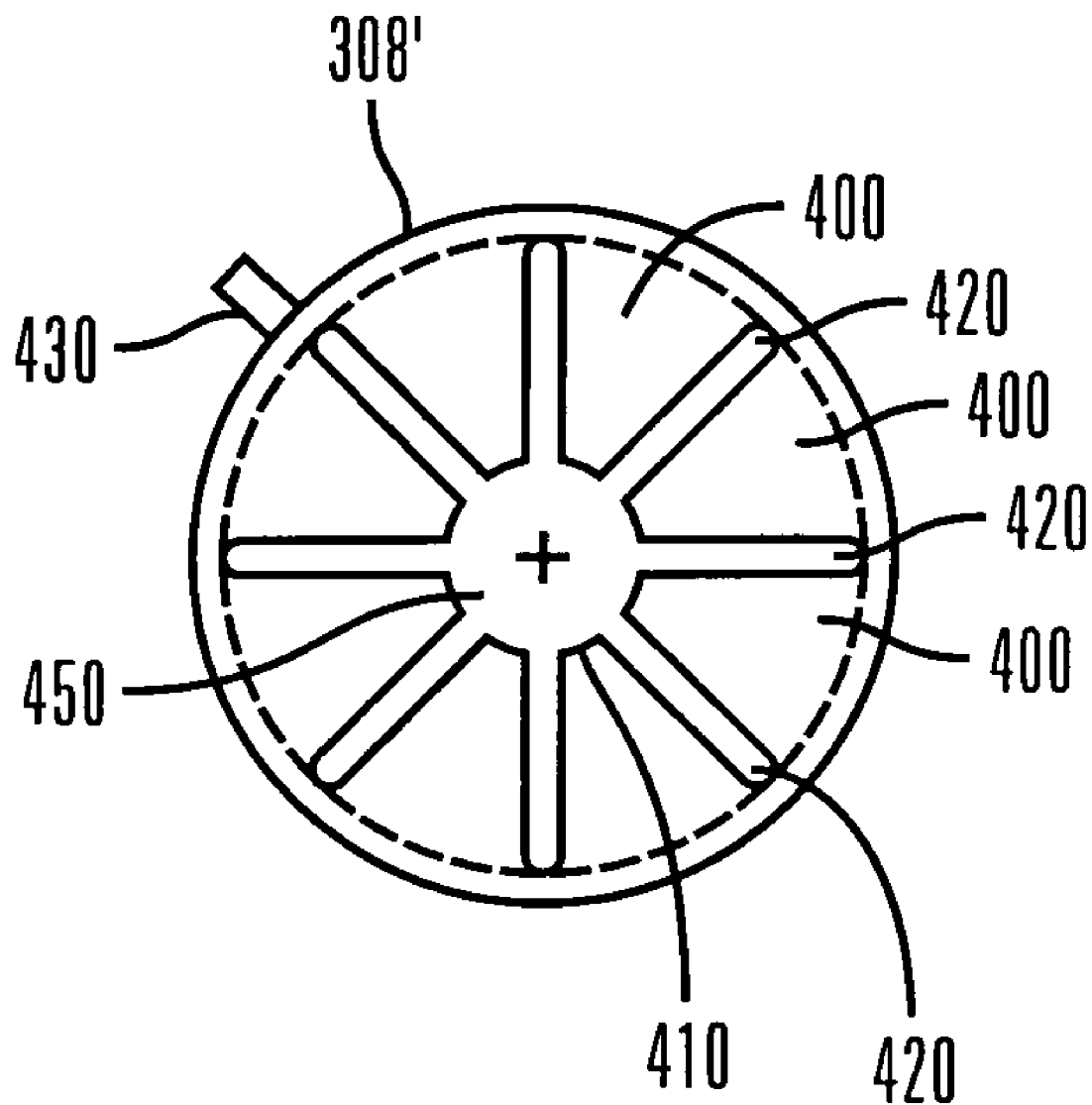
FIG. 9 is a cross-sectional end view of an alternative locking mechanism in accordance with another embodiment of the present invention.

In alternative embodiments of the present invention, different engagement arrangements between the plunger and the lead screw may be used, where some examples were given above with regards to multiple legs. In further alternative embodiments, the plunger could have a special adaptor at the end to fit directly upon the lead screw 302. For example, FIG. 9 is a cross-sectional end view of an alternative locking mechanism in accordance with another embodiment of the present invention. As seen in FIG. 9, the engaging end of the plunger rod 308' is comprised of a plurality of flexible segments 400, separated by hollow spokes 420. Each end 410 of the flexible segment 400 is a small nut thread segment. The collective ends 410 of the plurality of flexible segments 400 form a functional whole nut 450. The functional whole nut 450 is used to engage the plunger rod 308' directly onto the lead screw 302. In this engagement design, there would not need to be a camming receptacle to engage the end of the plunger rod 308'. Instead, the functional whole nut 450 is forced over the lead screw 302 to a starting delivery location. By pressing the plunger rod 308' over the lead screw, the flexible segments 400 are able to bend axially (with the aid of the hollow spokes 420, which allow the individual segments 400 to flex) to allow the functional whole nut 450 to fit over the lead screw 302, but resilient enough to bend back to their initial position to form the functional whole nut 450 over the lead screw 302 in an engaged position. Thus, the plunger rod 308' is compressed locked onto the lead screw 302 using the flexible segments 400. In other words, sliding the plunger over the lead screw quickly provides the needed force to bend the flexible segments 400, but then when the lead screw 302 moves more slowly, the force is insufficient to bend the flexible segments 400. In this alternative design, there would also be a need for an anti-rotation feature such as stopper 430 that travels with or against the nut 450 for the entire length of the lead screw 302 to ensure that the plunger rod 308' moves in conjunction with the lead screw 302. The stopper 430 would lock the plunger rod 308' to the lead screw 302 once the plunger rod 308' is properly installed upon the lead screw 302. In alternative embodiments, the flexible segments 400 may be replaced by other shapes, such as cilia shaped engaging members (e.g. numerous small flexible segments). In addition, alternative embodiments may have the flexible segments form a functional half nut rather than a whole nut 450. Thus, many variations can exist. For example, the forcing mechanism can be part of the cap structure used to load the reservoir 303 within the reservoir compartment 50. In addition, the reservoir may have to be hydraulically locked up during the insertion of the plunger 320 onto the lead screw 302, in order to prevent the plunger 320 from expelling fluid out from the nose end while installing a filled reservoir into the infusion device.

Therefore, while the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A reservoir for use with a medication infusion device having a rotatable lead screw with uniform thread size throughout the length of the lead screw for controllably dispensing fluid from the reservoir, the reservoir comprising:
   a hollow reservoir barrel adapted for receiving and supporting a supply of the fluid; and
   a reservoir plunger slidably received into the barrel and movable within the barrel to deliver the fluid from the barrel;
   wherein the reservoir plunger includes at least two radially flexible legs and an integral split nut connector that comprises at least a threaded partial nut formed at the end of each leg of the plunger such that the plunger is configured to engage the uniform thread sized lead screw between the at least two legs and the threaded partial nut on each leg can simultaneously engage the lead screw when the legs are compressed radially inwards to form a whole nut on the lead screw; and wherein the at least two radially flexible legs have arched surfaces to provide flexibility in the radial direction and rigidity in the axial direction.

2. The reservoir according to claim 1, wherein the partial nuts are engaged to the lead screw by a camming receptacle, wherein the camming receptacle has camming surfaces to press the partial nuts together to form a whole nut over the lead screw when the plunger is twisted within the camming receptacle.

3. The reservoir according to claim 2, wherein the plunger is twisted a quarter-turn to engage the lead screw and keep the plunger engaged to the lead screw.

4. The reservoir according to claim 3, wherein the plunger is twisted in a reverse direction to disengage the lead screw and allow removal of the reservoir.

5. The reservoir according to claim 1, wherein a locking cap is used to lock the reservoir inside the medication infusion device and to engage the reservoir to the lead screw.

6. The reservoir according to claim 5, wherein the cap allows the medication infusion device to be water resistant.

7. The reservoir according to claim 1, wherein the reservoir can be engaged to the lead screw with the reservoir being at any fill level.

8. The reservoir according to claim 1, wherein the medication infusion device has a unidirectional drive system.

9. The reservoir according to claim 1, wherein the integral split nut is surrounded by flexible members which allow the split nut to be forced over the lead screw to a starting position.

10. An infusion device system comprising:
a reservoir having a reservoir barrel adapted to be filled with a fluid, and a reservoir plunger slidably received into the barrel and movable within the barrel to deliver the fluid from the barrel, and
an infusion device including a device housing defining a reservoir compartment for receiving and supporting the reservoir, and drive means for engaging and controllably moving the plunger to deliver the fluid from the reservoir, the drive means including a rotatably driven lead screw;

wherein the reservoir plunger includes at least two radially flexible legs and an integral split nut connector that comprises at least a partial nut formed at the end of each leg of the plunger such that the plunger is adapted to permit the lead screw to fit between the at least two legs and the partial nut on each leg can simultaneously engage the lead screw when the legs are compressed radially to form a whole nut on the lead screw, wherein the lead screw has uniform thread size throughout the length of the lead screw; and wherein the partial nuts are engaged to the lead screw by a camming receptacle, wherein the camming receptacle has camming surfaces to press the partial nuts together to form a whole nut over the lead screw when the plunger is twisted within the camming receptacle.

11. The system according to claim 10, wherein the plunger is twisted a quarter-turn to engage the lead screw and keep the plunger engaged to the lead screw.

12. The system according to claim 11, wherein the plunger is twisted in a reverse direction to disengage the lead screw and allow removal of the reservoir.

13. The system according to claim 10, wherein a locking cap is used to lock the reservoir inside the medication infusion device and to engage the reservoir to the lead screw.

14. The system according to claim 13, wherein the cap allows the medication infusion device to be water resistant.

15. The system according to claim 10, wherein the reservoir can be engaged to the lead screw with the reservoir being at any fill level.

16. The system according to claim 10, wherein the medication infusion device has a unidirectional drive system.

17. The system according to claim 10, wherein the integral split nut is surrounded by flexible members which allow the split nut to be forced over the lead screw to a staffing position.

* * * * *